US008350229B2

(12) United States Patent
Watanabe

(10) Patent No.: US 8,350,229 B2
(45) Date of Patent: Jan. 8, 2013

(54) FLUORESCENCE OBSERVATION APPARATUS

(75) Inventor: Toshiaki Watanabe, Tokyo (JP)

(73) Assignee: Olympus Corporation, Tokyo (JP)

( * ) Notice: Subject to any disclaimer, the term of this patent is extended or adjusted under 35 U.S.C. 154(b) by 245 days.

(21) Appl. No.: 12/952,398

(22) Filed: Nov. 23, 2010

(65) Prior Publication Data

US 2011/0121200 A1 May 26, 2011

(30) Foreign Application Priority Data

Nov. 26, 2009 (JP) ................................. 2009-269156

(51) Int. Cl.
*G01J 1/58* (2006.01)
(52) U.S. Cl. .................................. 250/458.1; 250/459.1
(58) Field of Classification Search ................ 250/458.1, 250/459.1
See application file for complete search history.

(56) References Cited

U.S. PATENT DOCUMENTS 7,102,142 B2 * 9/2006 Sendai ....................... 250/461.1
7,978,258 B2 * 7/2011 Christiansen et al. ........ 348/364
2008/0015446 A1 1/2008 Mahmood et al.
2008/0309929 A1 * 12/2008 Christiansen et al. ..... 356/243.1
2009/0045351 A1 * 2/2009 Smolyaninov et al. .... 250/458.1

* cited by examiner

*Primary Examiner* — David Porta
*Assistant Examiner* — Mindy Vu
(74) *Attorney, Agent, or Firm* — Scully Scott Murphy & Presser, PC

(57) ABSTRACT

A quantitative fluorescence image and appropriate brightness is acquired and observed. Provided is a fluorescence observation apparatus including: an illumination section that includes a light source for irradiating an observation target region with illumination light and excitation light; a fluorescence image acquisition section that acquires a fluorescence image from fluorescence produced in the observation target region; a white-light image acquisition section that acquires a reference image from return light returning from the observation target region; an exposure-time adjustment unit that adjusts the exposure time based on the luminance value of the reference image; a diaphragm control section and a semiconductor laser control section that control the intensity of the illumination light and that of the excitation light based on the exposure time; a first normalization section that normalizes the luminance of the reference image and the fluorescence image by the exposure time; a second normalization section that normalizes the luminance of the reference image and the fluorescence image by the light intensity; and an image correction section that corrects the fluorescence image by the reference image, by using at least one of the normalized reference image or fluorescence image.

4 Claims, 12 Drawing Sheets

FLUORESCENCE OBSERVATION APPARATUS

BACKGROUND OF THE INVENTION

1. Field of the Invention

The present invention relates to a fluorescence observation apparatus.

This application is based on Japanese Patent Application No. 2009-269156, the content of which is incorporated herein by reference.

2. Description of Related Art

In a known conventional method, a fluorescence image is divided by a reference image to acquire a quantitative fluorescence image in which a change in fluorescence intensity, depending on observation distance, has been corrected (for example, see the specification of U.S. Patent Application Publication No. 2008/0015446). In a fluorescence observation apparatus disclosed in the specification of U.S. Patent Application Publication No. 2008/0015446, the exposure time of an image acquisition device is further adjusted automatically to allow a reflected-light image and a fluorescence image to be observed at constant brightness even if the observation conditions are changed.

However, as in the conventional fluorescence observation apparatus, if the brightness of an image is controlled just by adjusting the exposure time, there is a disadvantage that, in some cases, an image having appropriate brightness cannot be observed because an image becomes bright even if the exposure time is set to a lower limit, or the intensity of excitation light for irradiating an observation target region is too high, thus fading a fluorescent dye contained in a living body, making the fluorescence image dark. There is a case in that, if the intensity of irradiation light is changed through light adjustment, the corrected fluorescence image does not become quantitative because of an effect caused when the irradiation-light intensity of excitation light and the irradiation-light intensity of illumination light are changed.

BRIEF SUMMARY OF THE INVENTION

According to one aspect, the present invention provides a fluorescence observation apparatus including: an illumination section that includes a light source for irradiating a subject with illumination light and excitation light; a fluorescence image acquisition section that acquires a fluorescence image from fluorescence produced in the subject irradiated with the excitation light emitted from the illumination section; a return-light image acquisition section that acquires a reference image from return light returning from the subject irradiated with the illumination light emitted from the illumination section; an exposure-time adjustment section that adjusts exposure time based on a luminance value of the reference image acquired by the return-light image acquisition section; an illumination control section that controls the intensity of at least one of the illumination light and the excitation light emitted from the illumination section, based on the exposure time adjusted by the exposure-time adjustment section; first normalization section that normalizes the luminance of at least one of the reference image and the fluorescence image by the exposure time; second normalization section that normalizes the luminance of the at least one of the reference image and the fluorescence image by the intensity of the at least one of the illumination light and the excitation light controlled by the illumination control section; and an image correction section corrects the fluorescence image by the reference image, by using at least one of the reference image or the fluorescence image normalized by the first normalization section and the second normalization section.

According to the above-described aspect, when excitation light emitted from the illumination section irradiates a subject, the fluorescence image acquisition section acquires a fluorescence image from fluorescence produced in the subject; and, when illumination light emitted from the illumination section together with the excitation light irradiates the subject, the return-light image acquisition section acquires a reference image from return light of the illumination light.

In the fluorescence observation apparatus, when the luminance value of the reference image is high, the exposure-time adjustment section shortens the exposure time, and the illumination control section lowers the intensity of at least one of illumination light and excitation light based on that exposure time; thus, the intensities of illumination light and excitation light for irradiating the subject can be prevented from being too high, while suppressing the amount of incident light. On the other hand, when the luminance value of the reference image is low, the exposure-time adjustment section lengthens the exposure time, and the illumination control section raises the intensity of at least one of the illumination light and the excitation light based on that exposure time; thus, the intensities of the illumination light and excitation light for irradiating the subject can be prevented from being too low, while increasing the amount of the incident light.

Then, the first normalization section normalizes the luminance of at least one of the reference image and the fluorescence image by the exposure time adjusted by the exposure-time adjustment section, and the second normalization section normalizes the luminance of the at least one of the reference image and the fluorescence image by the intensity adjusted by the illumination control section; thus, the luminance value of the reference image and the luminance value of the fluorescence image can be normalized to have an approximately constant value irrespective of a change in exposure time or a change in light intensity. Therefore, when the image correction section corrects, using the reference image, the fluorescence image whose luminance value has been normalized, a change in fluorescence intensity, which depends on the distance traveled by the excitation light and the illumination light, can be accurately corrected. Thus, a quantitative and appropriate brightness fluorescence image can be acquired and observed.

In the above-described aspect, the image correction section may divide the fluorescence image by the reference image.

With this configuration, a high quantitative fluorescence image can be acquired through simple arithmetic processing.

In the above-described aspect, the exposure-time adjustment section may correct the exposure time such that the brightness of the at least one of the reference image acquired from the illumination light and the fluorescence image acquired from the excitation light, whose intensity has been controlled by the illumination control section, is maintained constant.

With this configuration, the brightness of the reference image and the fluorescence image can be maintained constant in accordance with the intensity of the illumination light and the intensity of the excitation light, which are controlled by the illumination control section.

In the above-described aspect, intensity correction section that corrects the intensity of the at least one of the reference image and the fluorescence image by which the luminance of the at least one of the illumination light and the excitation light is normalized by the second normalization section, based on the corresponding light intensity distribution characteristics may be further included.

When the intensity of the illumination light and the intensity of the excitation light are changed, the light intensity distribution characteristics of the illumination light and the light intensity distribution characteristics of the excitation light change in different ways from each other because of a difference in wavelength band between the illumination light and the excitation light. When the intensity correction section corrects the intensity of the illumination light and the intensity of the excitation light based on their intensity distribution characteristics, even if the illumination control section changes the intensities of the illumination light and the excitation light, the second normalization section can accurately normalize the luminance of the reference image and the fluorescence image to enhance the quantitativeness of the fluorescence image.

According to the present invention, an advantage is afforded in that a quantitative fluorescence image and appropriate brightness can be acquired and observed.

DETAILED DESCRIPTION OF THE INVENTION

First Embodiment

A fluorescence observation apparatus according to a first embodiment of the present invention will be described below with reference to the drawings.

Figure 1:
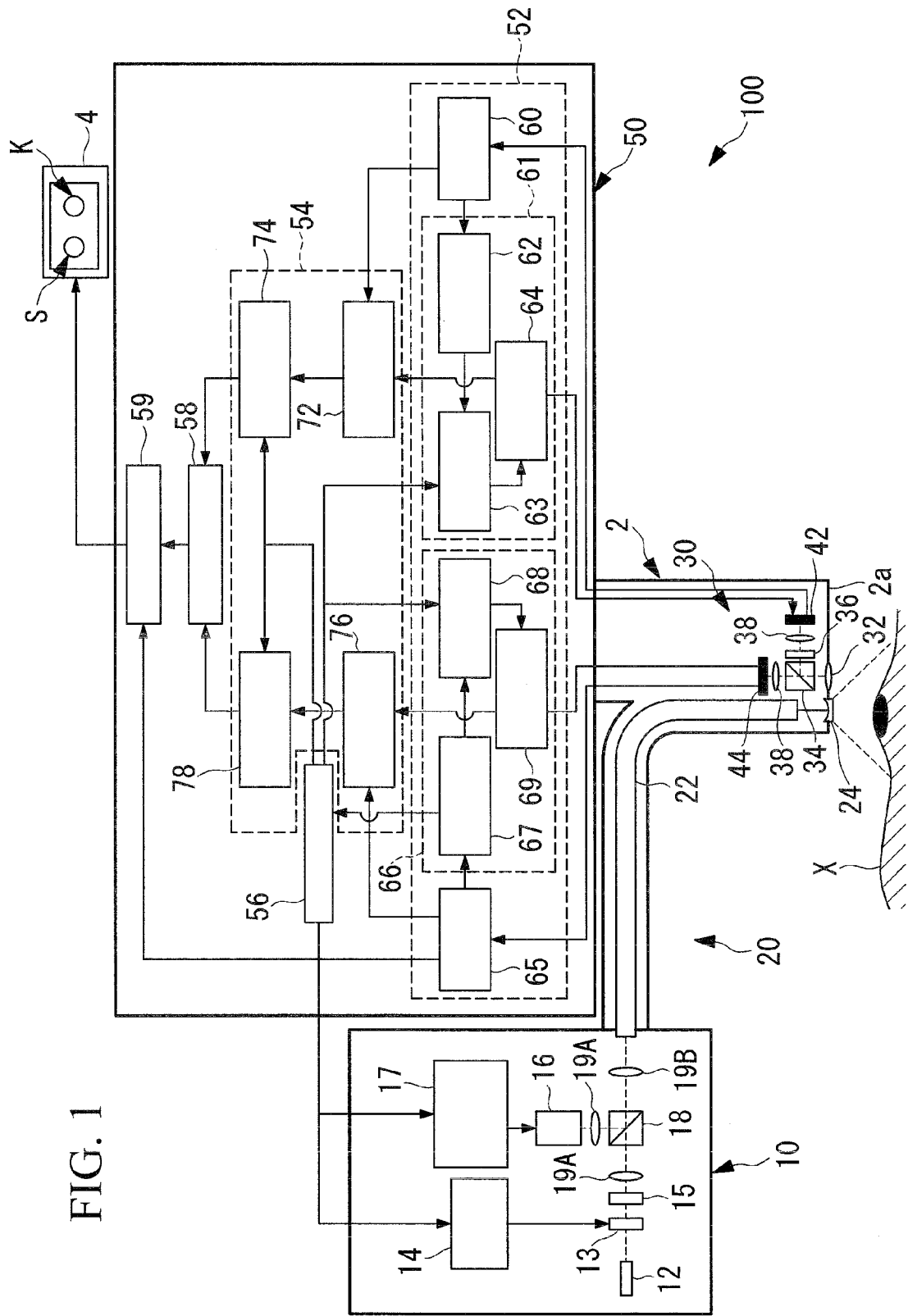
FIG. 1 is a block diagram showing, in outline, the configuration of a fluorescence observation apparatus according to a first embodiment of the present invention.

A fluorescence observation apparatus 100 according to this embodiment is a microscope apparatus and, as shown in FIG. 1, includes an elongated insertion portion 2 to be inserted into a body cavity, an illumination unit (illumination section) 20 provided with a light source 10 that outputs illumination light to be emitted from a tip 2a of the insertion portion 2, an image acquisition unit 30 that is disposed in the insertion portion 2 and that acquires image information of an observation target region X, which is a subject, an image processing section 50 that applies arithmetic processing to the image information acquired by the image acquisition unit 30, and a monitor 4 that displays an image processed by the image processing section 50 or other data.

The light source 10 includes a xenon lamp 12 that emits illumination light, a diaphragm 13 that restricts the amount of illumination light emitted from the xenon lamp 12, a diaphragm control section (illumination control section) 14 that adjusts an aperture range of the diaphragm 13, an infrared-light cut filter 15 that blocks infrared light in the illumination light passing through the diaphragm 13 and transmits only white light, a semiconductor laser 16 that emits excitation light having a wavelength band of 740 nm, a semiconductor laser control section (illumination control section) 17 that controls the output power of the semiconductor laser 16, and a first beam splitter 18 that transmits the white light coming from the infrared-light cut filter 15 and reflects the excitation light coming from the semiconductor laser 16 to guide the white light and the excitation light to the same optical path.

The diaphragm control section 14 changes the aperture range of the diaphragm 13 to change the amount of illumination light passing through the diaphragm 13, thus controlling the intensity of illumination light.

The semiconductor laser control section 17 varies the output power of the semiconductor laser 16, thus controlling the intensity of excitation light.

The infrared-light cut filter 15 transmits only white light having a wavelength band of 400 to 680 nm, for example. Reference symbol 19A denotes a first coupling lens that converges the white light transmitted through the infrared-light cut filter 15 and a first coupling lens that converges the excitation light emitted from the semiconductor laser 16. Reference symbol 19B denotes a second coupling lens that converges the white light and the excitation light that are guided to the same optical path by the first beam splitter 18.

The illumination unit 20 is disposed along substantially the whole length in a longitudinal direction of the insertion portion 2 and includes a light guide fiber 22 that guides the white light and the excitation light converged by the second coupling lens 19B to the tip 2a of the insertion portion 2 and a beam-spreading lens 24 that is disposed at the tip 2a of the insertion portion 2 and that spreads the white light and the excitation light guided by the light guide fiber 22 to irradiate the observation target region X with them.

The image acquisition unit 30 includes an objective lens 32 that collects return light returning from the observation target region X irradiated with the white light and the excitation light by the illumination unit 20 and a second beam splitter 34 that reflects, of the return light collected by the objective lens 32, light (excitation light and fluorescence) having an excitation wavelength or longer and that transmits white light having a wavelength shorter than the excitation wavelength. The objective lens 32 is disposed beside the beam-spreading lens 24 at the tip 2a of the insertion portion 2.

The image acquisition unit 30 further includes an excitation-light cut filter 36 that blocks, of the excitation light and the fluorescence reflected at the second beam splitter 34, the excitation light and transmits only the fluorescence (for example, near-infrared fluorescence) therethrough; two focusing lenses 38 that respectively converge the fluorescence transmitted through the excitation-light cut filter 36 and the white light transmitted through the second beam splitter 34; a fluorescence image acquisition section 42 that acquires an image of the fluorescence converged by the focusing lens 38 to acquire fluorescence image information; and a white-light image acquisition section (return-light image acquisition section) 44 that acquires an image of the white light converged by the focusing lens 38 to acquire reference image information.

The excitation-light cut filter 36 transmits therethrough only fluorescence having a wavelength band of 765 to 850 nm, for example.

The fluorescence image acquisition section 42 is, for example, a monochrome CCD sensitive to the fluorescence. The white-light image acquisition section 44 is, for example, a color CCD for white light and includes a mosaic filter (not shown).

The image processing section 50 includes an image acquisition unit 52 that adjusts the exposure time of the fluorescence image acquisition section 42 and the white-light image acquisition section 44 and acquires a fluorescence image and a reference image, a luminance normalization unit 54 that normalizes the luminance of the fluorescence image and the reference image acquired by the image acquisition unit 52, a quantitativeness control section 56 that controls the quantitativeness of the fluorescence image and the reference image, and a division processing section (image correction section) 58 that uses the fluorescence image and the reference image normalized by the luminance normalization unit 54 to correct the fluorescence image by the reference image.

The image acquisition unit 52 includes a fluorescence image generation section 60 that generates a two-dimensional fluorescence image from the fluorescence image information acquired by the fluorescence image acquisition section 42, a fluorescence exposure-time adjustment unit (exposure-time adjustment section) 61 that adjusts the exposure time of the fluorescence image acquisition section 42, a reference image generation section 65 that generates a two-dimensional reference image from the reference image information acquired by the white-light image acquisition section 44, and a white-light exposure-time adjustment unit (exposure-time adjustment section) 66 that adjusts the exposure time of the white-light image acquisition section 44.

The fluorescence exposure-time adjustment unit 61 includes a fluorescence exposure-time calculating section 62 that calculates the exposure time for the next frame of the fluorescence image acquisition section 42 based on the luminance value of the fluorescence image generated by the fluorescence image generation section 60, a fluorescence exposure-time correcting section 63 that corrects the exposure time by multiplying the exposure time for the next frame calculated by the fluorescence exposure-time calculating section 62 by a predetermined correction factor, and a fluorescence exposure-time control section 64 that controls the exposure time of the fluorescence image acquisition section 42 based on the exposure time corrected by the fluorescence exposure-time correcting section 63.

Similarly, the white-light exposure-time adjustment unit 66 includes a white-light exposure-time calculating section 67 that calculates the exposure time for the next frame of the white-light image acquisition section 44 based on the luminance value of the reference image generated by the reference image generation section 65, a white-light exposure-time correcting section 68 that corrects the exposure time by multiplying the exposure time for the next frame calculated by the white-light exposure-time calculating section 67 by a predetermined correction factor, and a white-light exposure-time control section 69 that controls the exposure time of the white-light image acquisition section 44 based on the exposure time corrected by the white-light exposure-time correcting section 68.

As the luminance value of the fluorescence image and the luminance value of the reference image, for example, the average value of luminance values in a predetermined region of the fluorescence image and that of the reference image are used, respectively.

The luminance normalization unit 54 includes a fluorescence-image first normalization section (first normalization section) 72 that divides the luminance of the fluorescence image generated by the fluorescence image generation section 60 by the exposure time of the fluorescence image acquisition section 42, a fluorescence-image second normalization section (second normalization section) 74 that further normalizes, by the intensity of excitation light, the luminance of the fluorescence image that has been normalized by the exposure time by the fluorescence-image first normalization section 72, a reference-image first normalization section (first normalization section) 76 that divides the luminance of the reference image generated by the reference image generation section 65 by the exposure time of the white-light image acquisition section 44, and a reference-image second normalization section (second normalization section) 78 that further normalizes, by the intensity of illumination light, the luminance of the reference image that has been normalized by the exposure time by the reference-image first normalization section 76.

Figure 2:
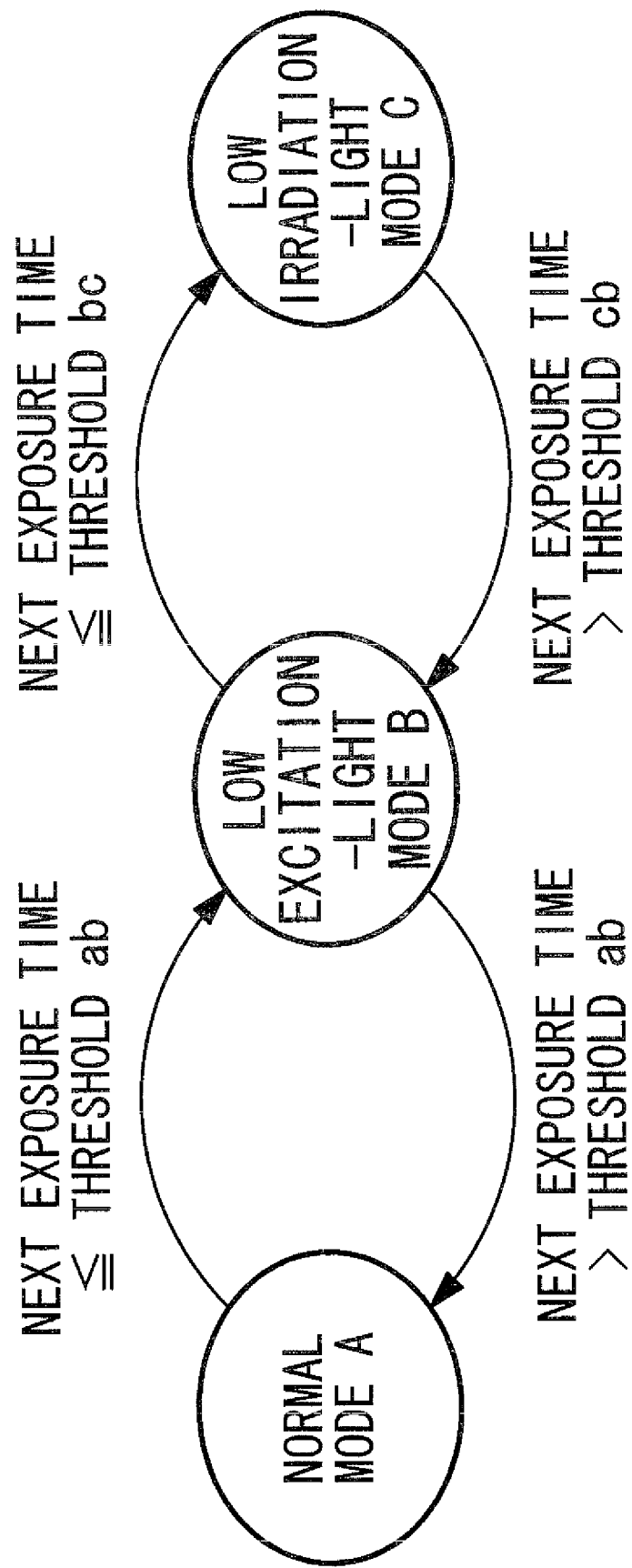
FIG. 2 is a diagram showing example control modes provided in a quantitativeness control section shown in FIG. 1.

As shown in FIG. 2, the quantitativeness control section 56 has three control modes, i.e., a normal mode A in which the intensity of illumination light and the intensity of excitation light are normal, a low excitation-light mode B in which only the intensity of excitation light is low, and a low irradiation-light mode C in which not only the intensity of excitation light but also the intensity of illumination light is low.

The quantitativeness control section 56 reads the exposure time for the next frame of the white-light image acquisition section 44 calculated by the white-light exposure-time calculating section 67 and specifies a control mode in the diaphragm control section 14 and the semiconductor laser control section 17. The quantitativeness control section 56 inputs the control mode specified in the semiconductor laser control section 17 to the fluorescence-image second normalization section 74 to specify the intensity of excitation light by which the luminance of the fluorescence image is divided, and inputs the control mode specified in the diaphragm control section 14 to the reference-image second normalization section 78 to specify the intensity of illumination light by which the luminance of the reference image is divided.

When the quantitativeness control section 56 changes the control mode in the diaphragm control section 14, the quantitativeness control section 56 specifies a correction factor in the fluorescence exposure-time correcting section 63 such that the brightness between fluorescence images acquired before and after the intensity of excitation light is changed is maintained constant.

The division processing section 58 divides the fluorescence image normalized by the fluorescence-image second normalization section 74 by the reference image normalized by the reference-image second normalization section 78 to acquire a corrected fluorescence image K.

The image processing section 50 further includes an image composition section 59 that generates an image by combining a reference image S generated by the reference image generation section 65 and the corrected fluorescence image K generated by the division processing section 58. The image composition section 59 combines the reference image S and the corrected fluorescence image K and arranges and displays them side-by-side on the monitor 4 at the same time. The image composition section 59 may have a density conversion table in which the luminance value of the corrected fluorescence image K is associated with the abundance of fluorescence (that is, the concentration of fluorescence agent) and display, on the monitor 4, the fluorescence density in a particular region.

The operation of the thus-configured fluorescence observation apparatus 100 according to this embodiment will be described.

To observe the observation target region X in the body cavity of a living body, for example, by using the fluorescence observation apparatus 100 of this embodiment, the insertion portion 2 is inserted into the body cavity, and the tip 2a thereof is made to face the observation target region X.

Then, the light source 10 is operated. Of illumination light emitted from the xenon lamp 12 and passing through the diaphragm 13, white light transmitted through the infrared-light cut filter 15 is converged by the first coupling lens 19A and is transmitted through the first beam splitter 18. Excitation light emitted from the semiconductor laser 16 is converged by the first coupling lens 19A and is reflected at the first beam splitter 18. This white light and excitation light are both converged by the second coupling lens 19B and enter the light guide fiber 22.

The white light and the excitation light entering the light guide fiber 22 are guided to the tip 2a of the insertion portion 2 and are spread by the beam-spreading lens 24, thus irradiating the observation target region X. In the observation target region X, a fluorescent substance contained therein is excited by the excitation light to emit fluorescence, and part of the white light and the excitation light is reflected at a surface of the observation target region X.

The fluorescence and the return-light portion of the excitation light and the white light are collected by the objective lens 32 of the insertion portion 2 and are branched into respective wavelengths by the second beam splitter 34. Specifically, in the second beam splitter 34, light having an excitation wavelength or longer, namely, the excitation light and the fluorescence, are reflected thereat, and the white light having a wavelength shorter than the excitation wavelength is transmitted therethrough.

From the excitation light and the fluorescence reflected at the second beam splitter 34, the excitation light is removed by the excitation-light cut filter 36, and only the fluorescence is converged by the focusing lens 38. Then, the fluorescence image acquisition section 42 acquires an image of the fluorescence to acquire fluorescence image information.

The white light transmitted through the second beam splitter 34 is converged by the focusing lens 38, and the white-light image acquisition section 44 acquires an image of the white light to acquire reference image information.

The fluorescence image information and the reference image information may be acquired at different timing or at the same time.

The fluorescence image information acquired by the fluorescence image acquisition section 42 and the reference image information acquired by the white-light image acquisition section 44 are each input to the image processing section 50 and subjected to image processing.

In the image processing section 50, the fluorescence image information is input to the fluorescence image generation section 60, and a two-dimensional fluorescence image is generated therefrom. In this case, the fluorescence exposure-time calculating section 62 calculates the exposure time for the next frame of the fluorescence image acquisition section 42 based on the luminance value of the fluorescence image generated by the fluorescence image generation section 60. Then, the calculated exposure time of the fluorescence image acquisition section 42 is input to the fluorescence exposure-time control section 64 via the fluorescence exposure-time correcting section 63 and is specified therein.

Similarly, the reference image information is input to the reference image generation section 65, and a two-dimensional reference image is generated therefrom. In this case, the white-light exposure-time calculating section 67 calculates the exposure time for the next frame of the white-light image acquisition section 44 based on the luminance value of the reference image generated by the reference image generation section 65. Then, the calculated exposure time of the white-light image acquisition section 44 is input to the white-light exposure-time control section 69 via the white-light exposure-time correcting section 68 and is specified therein.

The fluorescence image generated by the fluorescence image generation section 60 and the reference image generated by the reference image generation section 65 are each sent to the luminance normalization unit 54.

In the luminance normalization unit 54, the fluorescence-image first normalization section 72 reads the exposure time of the fluorescence image acquisition section 42 from the fluorescence exposure-time control section 64 and divides the luminance value of the fluorescence image by the exposure time. Thus, the difference in exposure time of the fluorescence image is normalized, and thus the fluorescence image has a normalized luminance value per unit time.

Similarly, the reference-image first normalization section 76 reads the exposure time of the white-light image acquisition section 44 from the white-light exposure-time control section 69 and divides the luminance value of the reference image by the exposure time. Thus, the difference in exposure time of the reference image is normalized, and thus the reference image has a normalized luminance value per unit time.

Next, the fluorescence image normalized by the exposure time by the fluorescence-image first normalization section 72 is sent to the fluorescence-image second normalization section 74, and the reference image normalized by the exposure time by the reference-image first normalization section 76 is sent to the reference-image second normalization section 78.

In the fluorescence-image second normalization section 74, the luminance value of the fluorescence image is divided by the intensity of excitation light controlled by the semiconductor laser control section 17, based on the control mode output from the quantitativeness control section 56. Thus, the difference in light intensity of the fluorescence image is normalized, and thus the fluorescence image has a normalized luminance value per unit excitation-light intensity.

Similarly, in the reference-image second normalization section 78, the luminance value of the reference image is divided by the intensity of white light controlled by the diaphragm control section 14, based on the control mode output from the quantitativeness control section 56. Thus, the difference in light intensity of the reference image is normalized, and thus the reference image has a normalized luminance value per unit white-light intensity.

In the fluorescence observation apparatus 100 of this embodiment, the exposure time for the next frame of the white-light image acquisition section 44 calculated by the white-light exposure-time calculating section 67 is input to the quantitativeness control section 56, and the quantitativeness control section 56 controls the quantitativeness of the fluorescence image and the reference image. Specifically, as shown in flowcharts of FIGS. 3, 4, and 5, when the quantitativeness control section 56 receives the exposure time for the next frame of the white-light image acquisition section 44 from the white-light exposure-time calculating section 67 (Step S1), control is performed as follows according to the current control mode.

Figure 3:
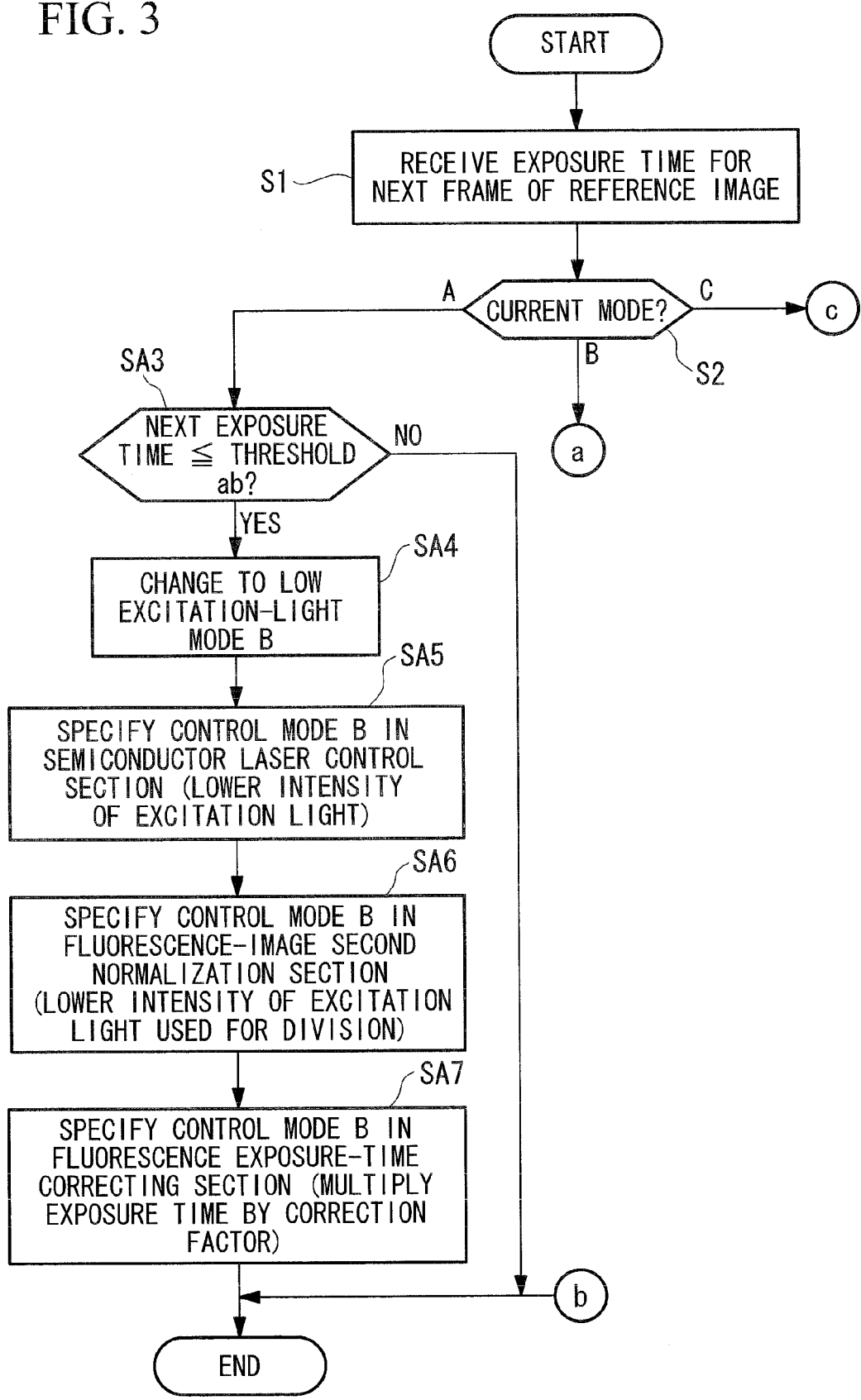
FIG. 3 is a flowchart showing a quantitativeness control procedure starting from a normal mode, performed by the quantitativeness control section shown in FIG. 1.
Figure 6:
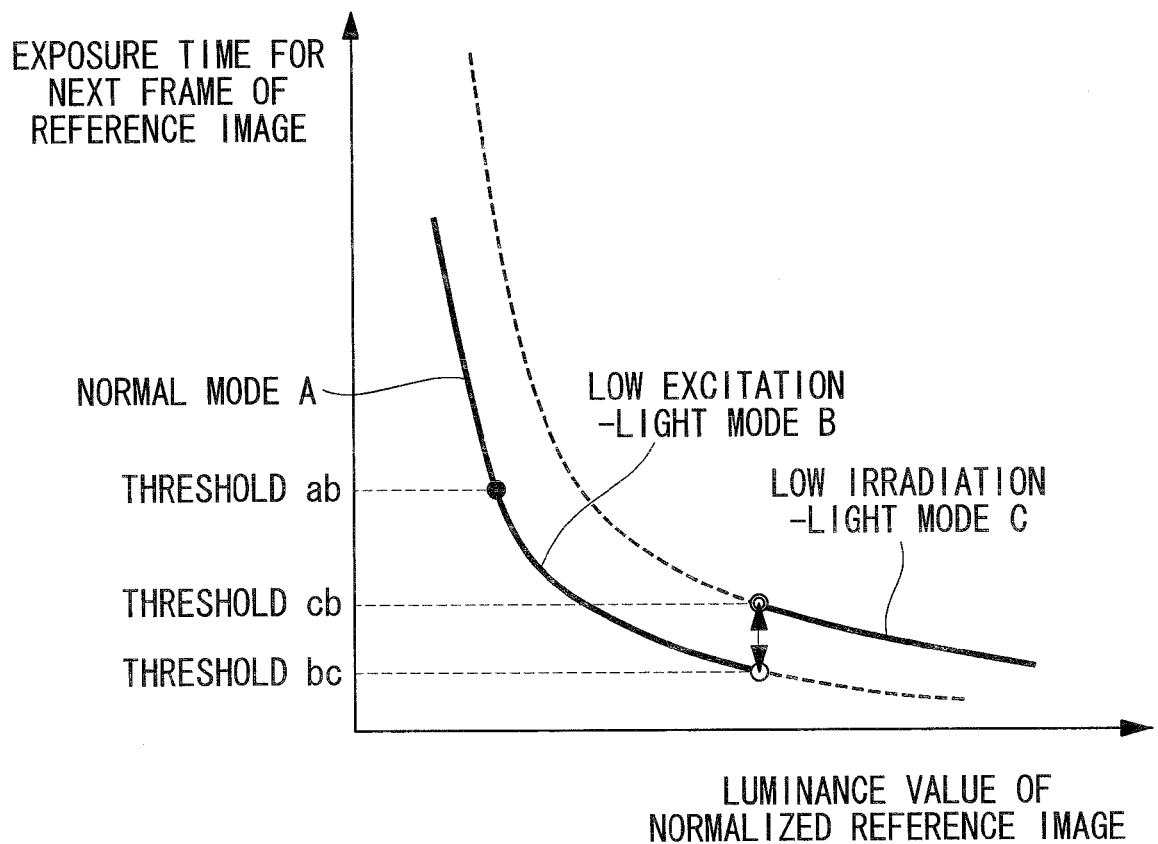
FIG. 6 is a diagram showing the relationships between the normal mode and the low excitation-light mode and between the low excitation-light mode and the low irradiation-light mode, selected by the quantitativeness control section shown in FIG. 1.

If the current control mode is the normal mode A ("A" in Step S2), as shown in FIG. 3, it is first determined whether the exposure time for the next frame of the white-light image acquisition section 44 is shorter than or equal to a threshold ab (Step SA3). If the exposure time for the next frame is longer than the threshold ab ("NO" in Step SA3), the normal mode A is maintained (end), as shown in FIG. 6. On the other hand, if the exposure time for the next frame is shorter than or equal to the threshold ab ("YES" in Step SA3), the control mode is changed to the low excitation-light mode B (Step SA4).

In this case, the quantitativeness control section 56 outputs to the semiconductor laser control section 17 a control signal for switching to the low excitation-light mode B, and the semiconductor laser control section 17 reduces the output power of the semiconductor laser 16 to lower the intensity of excitation light (Step SA5). Here, when the exposure time for the next frame of the white-light image acquisition section 44 is short, this means that the intensity of white light for irradiating the observation target region X is high, and it is conceivable that the tip 2a of the insertion portion 2 and the observation target region X are too close. Therefore, by lowering the intensity of the excitation light, the intensity of the excitation light for irradiating the observation target region X can be prevented from being too high.

In accordance with the lowering of the intensity of the excitation light, the quantitativeness control section 56 outputs to the fluorescence-image second normalization section 74 the control signal for switching to the low excitation-light mode B to lower the intensity of the excitation light by which the luminance value of the fluorescence image is divided (Step SA6). Thus, the quantitativeness of the normalized fluorescence image can be maintained in the fluorescence-image second normalization section 74.

The quantitativeness control section 56 further outputs to the fluorescence exposure-time correcting section 63 the control signal for switching to the low excitation-light mode B and specifies a correction factor for lengthening the exposure time for the next frame of the fluorescence image acquisition section 42 in order that a fluorescence image to be acquired immediately after the intensity of the excitation light is lowered is not dark (Step SA7). By doing so, in the fluorescence exposure-time correcting section 63, the exposure time for the next frame of the fluorescence image acquisition section 42 specified by the fluorescence exposure-time control section 64 is corrected, and the brightness of the fluorescence image can be maintained substantially constant. In a case where a considerable time is required to change the intensity of the excitation light with respect to the exposure time, a correction factor may be specified with a change in the intensity of the excitation light taken into account.

Figure 4:
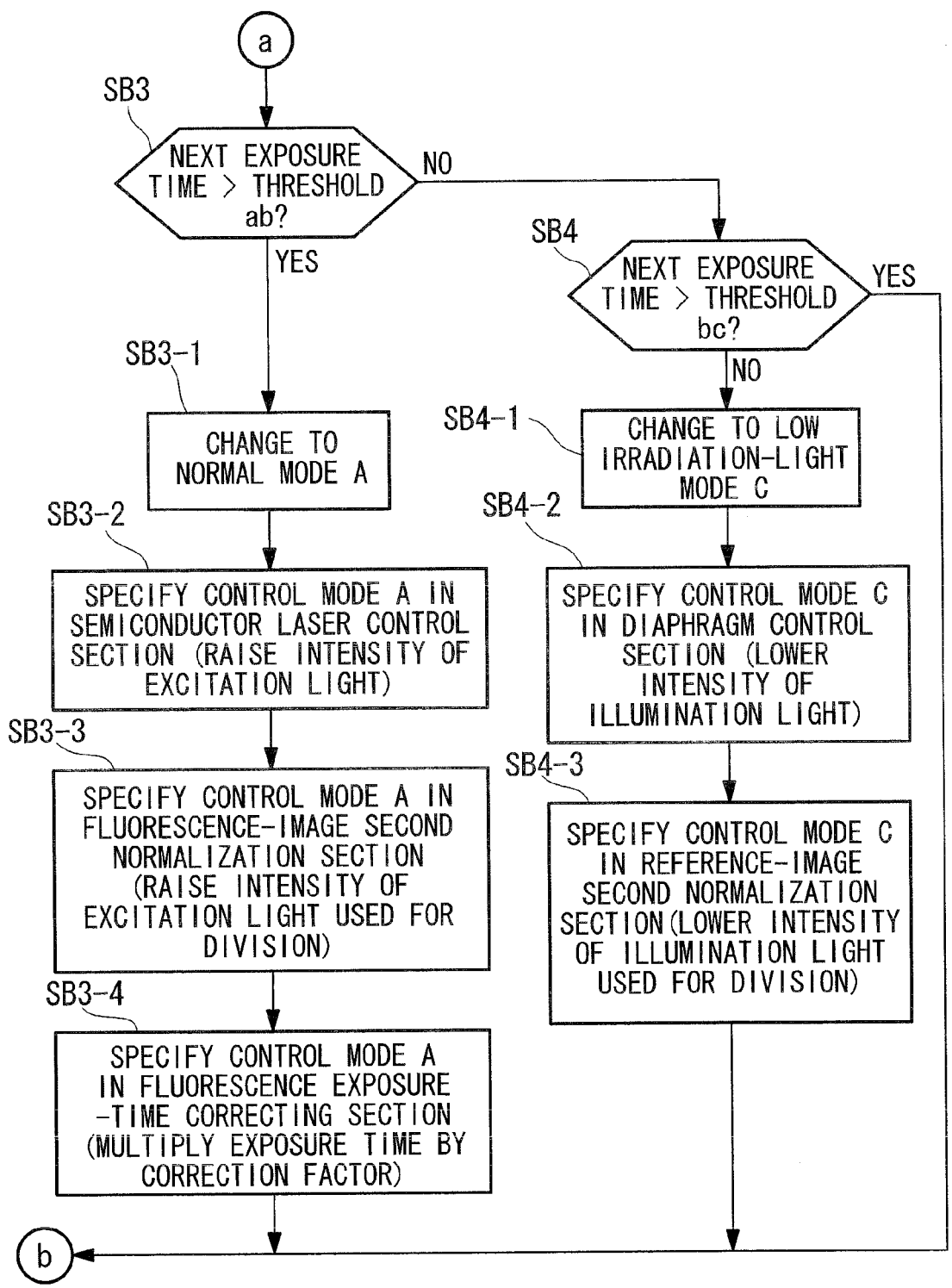
FIG. 4 is a flowchart showing a quantitativeness control procedure starting from a low excitation-light mode, performed by the quantitativeness control section shown in FIG. 1.

Next, if the current control mode is the low excitation-light mode B ("B" in Step S2), as shown in FIG. 4, it is determined whether the exposure time for the next frame of the white-light image acquisition section 44 is longer than the threshold ab (Step SB3). If the exposure time is longer than the threshold ab ("YES" in Step SB3), the control mode is changed to the normal mode A (Step SB3-1), as shown in FIG. 6.

In this case, the quantitativeness control section 56 outputs to the semiconductor laser control section 17 a control signal for switching to the normal mode A, and the semiconductor laser control section 17 increases the output power of the semiconductor laser 16 to raise the intensity of excitation light (Step SB3-2). In accordance with the raising of the intensity of the excitation light, the quantitativeness control section 56 outputs to the fluorescence-image second normalization section 74 the control signal for switching to the normal mode A to raise the intensity of the excitation light by which the luminance value of the fluorescence image is divided (Step SB3-3). Then, the quantitativeness control section 56 outputs to the fluorescence exposure-time correcting section 63 the control signal for switching to the normal mode A and specifies a correction factor for shortening the exposure time for the next frame of the fluorescence image acquisition section 42 in order that a fluorescence image to be acquired immediately after the intensity of the excitation light is raised will not be saturated (Step SB3-4).

On the other hand, if the exposure time for the next frame of the white-light image acquisition section 44 is shorter than or equal to the threshold ab ("NO" in Step SB3), it is determined whether the exposure time is longer than a threshold bc (Step SB4). If the exposure time for the next frame is longer than the threshold bc ("YES" in Step SB4), as shown in FIG. 6, the low excitation-light mode B is maintained (end). On the other hand, if the exposure time for the next frame is shorter than or equal to the threshold bc ("NO" in Step SB4), the control mode is changed to the low irradiation-light mode C (Step SB4-1).

In this case, the quantitativeness control section 56 outputs to the diaphragm control section 14 a control signal for switching to the low irradiation-light mode C, and the diaphragm control section 14 narrows the aperture range of the diaphragm 13 to lower the intensity of illumination light (Step SB4-2). By lowering the intensity of the illumination light, it is possible to prevent a situation in which the reference image is saturated to become white because the intensity of the white light for irradiating the observation target region X is too high.

In accordance with the lowering of the intensity of the illumination light, the quantitativeness control section 56 outputs to the reference-image second normalization section 78 the control signal for switching to the low irradiation-light mode C to lower the intensity of the illumination light by which the luminance value of the reference image is divided (Step SB4-3). By doing so, the quantitativeness of the normalized reference image can be maintained in the reference-image second normalization section 78.

Figure 5:
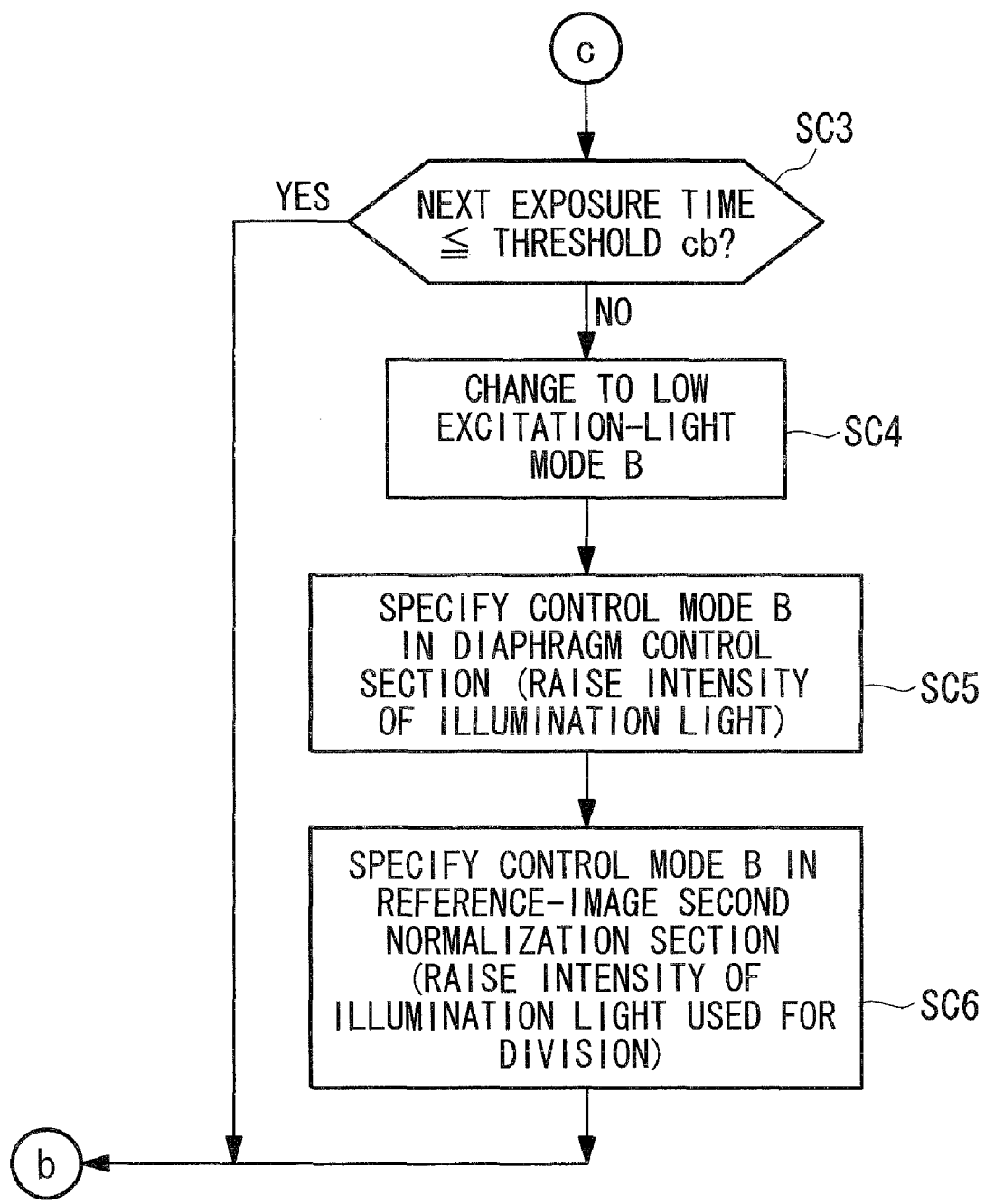
FIG. 5 is a flowchart showing a quantitativeness control procedure starting from a low irradiation-light mode, performed by the quantitativeness control section shown in FIG. 1.

Next, if the current control mode is the low irradiation-light mode C ("C" in Step S2), as shown in FIG. 5, it is determined whether the exposure time for the next frame of the white-light image acquisition section 44 is shorter than or equal to a threshold cb (Step SC3). If the exposure time is shorter than or equal to the threshold cb ("YES" in Step SC3), as shown in FIG. 6, the low irradiation-light mode C is maintained (end). On the other hand, if the exposure time is longer than the threshold cb ("NO" in Step SC3), the control mode is changed to the low excitation-light mode B (Step SC4).

In this case, the quantitativeness control section 56 outputs to the diaphragm control section 14 the control signal for switching to the low excitation-light mode B, and the diaphragm control section 14 expands the aperture range of the diaphragm 13 to raise the intensity of illumination light (Step SC5). By raising the intensity of the illumination light, it is possible to prevent a situation in which a reference image is too dark because the intensity of the white light for irradiating the observation target region X is too low.

In accordance with the raising of the intensity of illumination light, the quantitativeness control section 56 outputs to the reference-image second normalization section 78 the control signal for switching to the low excitation-light mode B to raise the intensity of the illumination light by which the luminance value of the reference image is divided (Step SC6). By doing so, the quantitativeness of the normalized reference image can be maintained in the reference-image second normalization section 78.

In this way, the fluorescence image and the reference image that have been normalized by the light intensity in the fluorescence-image second normalization section 74 and the reference-image second normalization section 78, respectively, which are controlled by the quantitativeness control section 56, are each sent to the division processing section 58. In the division processing section 58, the fluorescence image normalized by the exposure time and the light intensity is divided by the reference image, thereby canceling distance dependency and acquiring an accurately corrected quantitative fluorescence image K.

The corrected fluorescence image K acquired by the division processing section 58 is sent to the image composition section 59 and is combined with a reference image S read from the reference image generation section 65, and they are simultaneously displayed on the monitor 4. The fluorescence density in a particular region may be displayed on the monitor 4 based on the density conversion table.

As described above, according to the fluorescence observation apparatus 100 of this embodiment, the intensities of the excitation light and illumination light and the exposure time of the fluorescence image acquisition section 42 are changed based on the exposure time for the next frame of the white-light image acquisition section 44, that is, the luminance value of a next-frame reference image; thus, an image having appropriate brightness can be acquired while the appropriate intensities of the excitation light and illumination light for irradiating the observation target region X are maintained. Then, the fluorescence image whose luminance has been normalized by the exposure time and the light intensity is corrected by using the reference image, thereby accurately correcting a change in fluorescence intensity, which depends on the distance traveled by the excitation light, or the like. Thus, a quantitative and appropriate brightness fluorescence image can be acquired and observed.

In this embodiment, when the quantitativeness control section 56 changes the control mode in the diaphragm control section 14, the quantitativeness control section 56 may control the white-light exposure-time correcting section 68 such that the brightness between reference images acquired before and after the intensity of the illumination light is changed is maintained constant.

Second Embodiment

Next, a fluorescence observation apparatus according to a second embodiment of the present invention will be described.

Figure 7:
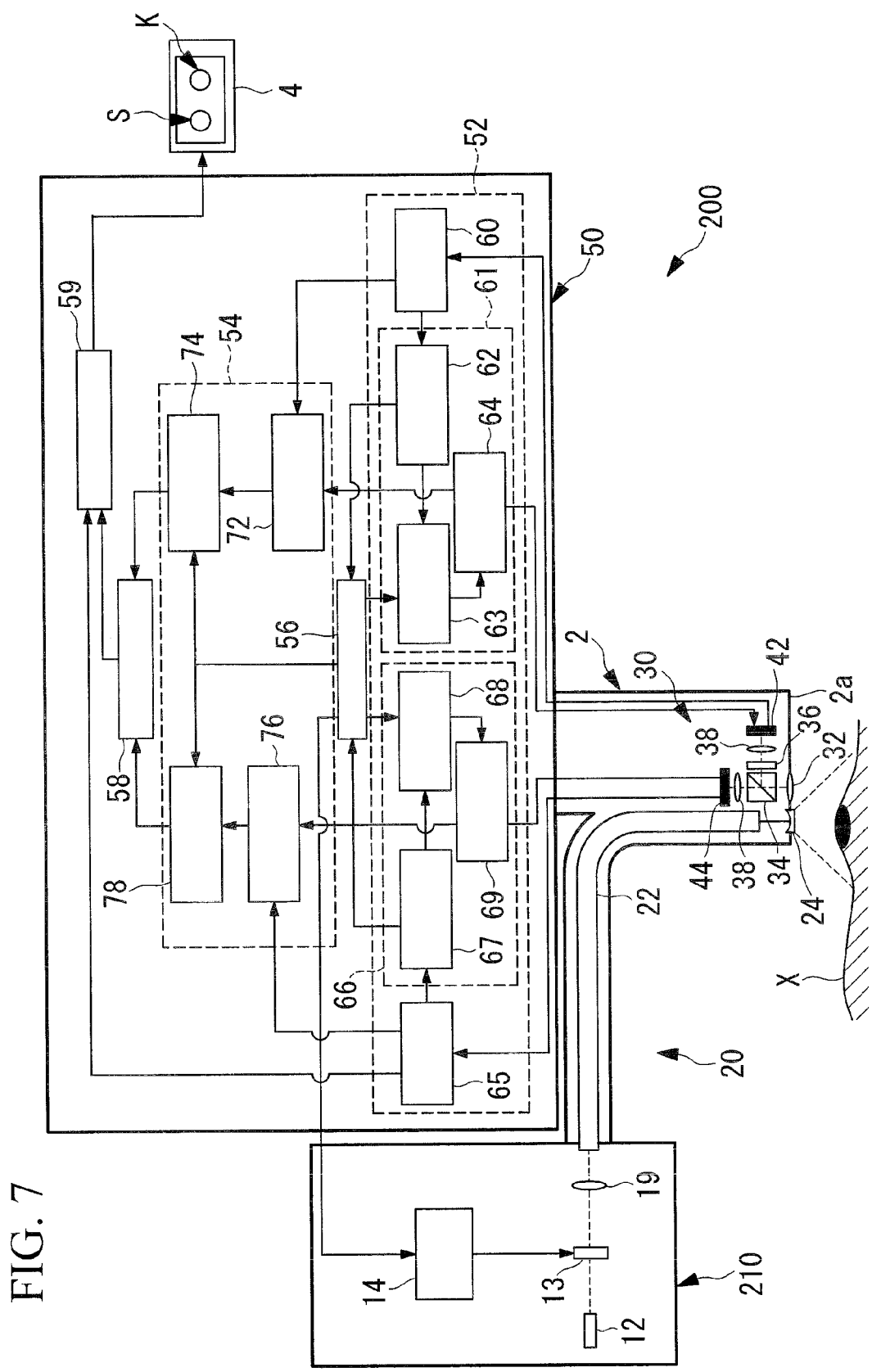
FIG. 7 is a block diagram showing, in outline, the configuration of a fluorescence observation apparatus according to a second embodiment of the present invention.

As shown in FIG. 7, a fluorescence observation apparatus 200 of this embodiment differs from that of the first embodiment in that a light source 210 is not provided with the semiconductor laser 16, and the diaphragm control section 14 simultaneously controls the amounts of illumination light and excitation light emitted from the xenon lamp 12.

Identical reference symbols are assigned to the component parts common to the fluorescence observation apparatus 100 of the first embodiment, and a description thereof will be omitted.

The light source 210 includes the xenon lamp 12, the diaphragm 13, and a coupling lens 19 that converges illumination light (white light), which includes excitation light emitted from the xenon lamp 12 and passing through the diaphragm 13.

Figure 8:
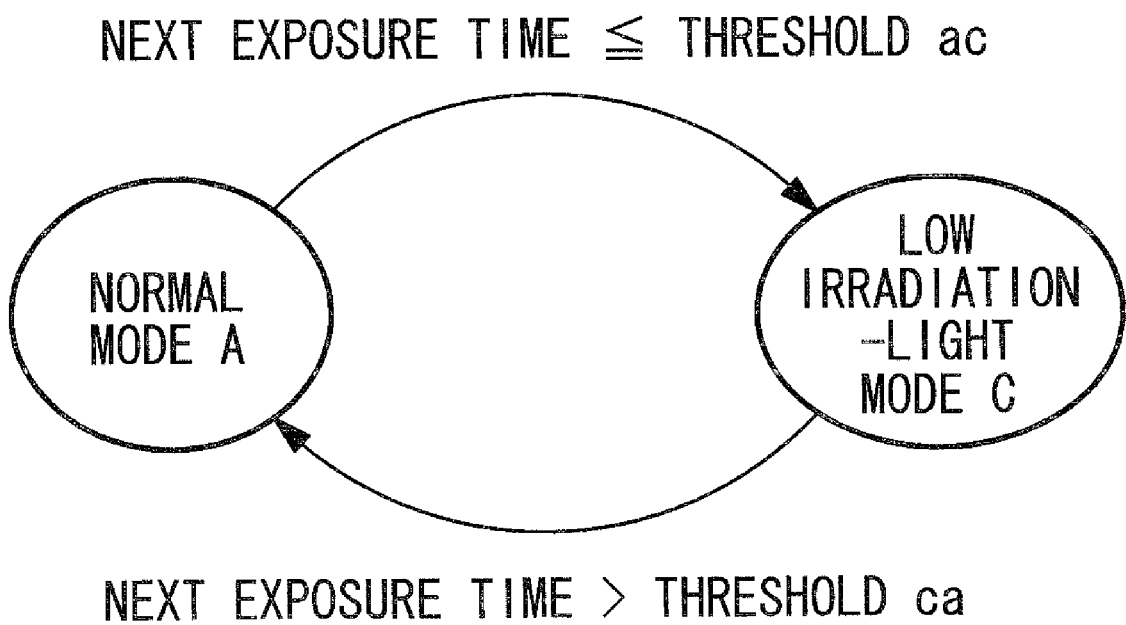
FIG. 8 is a diagram showing example control modes provided in a quantitativeness control section shown in FIG. 7.

As shown in FIG. 8, the quantitativeness control section 56 has two control modes, i.e., the normal mode A and the low irradiation-light mode C. The quantitativeness control section 56 reads the exposure time for the next frame of the white-light image acquisition section 44 calculated by the white-light exposure-time calculating section 67, specifies the control mode in the diaphragm control section 14, and inputs the control mode specified in the diaphragm control section 14 to the fluorescence-image second normalization section 74 and the reference-image second normalization section 78.

The operation of the thus-configured fluorescence observation apparatus 200 will now be described.

Illumination light that includes excitation light emitted from the xenon lamp 12, passing through the diaphragm 13, and converged by the coupling lens 19 is guided by the light guide fiber 22 to the tip 2a of the insertion portion 2 and irradiates the observation target region X. Fluorescence produced in the observation target region X is reflected at the second beam splitter 34 and is acquired by the fluorescence image acquisition section 42 as fluorescence image information; and white light returning from the observation target region X is transmitted through the second beam splitter 34 and is acquired by the white-light image acquisition section 44 as reference image information. Then, the fluorescence image information and the reference image information are each input to the image processing section 50 and subjected to image processing.

Figure 9:
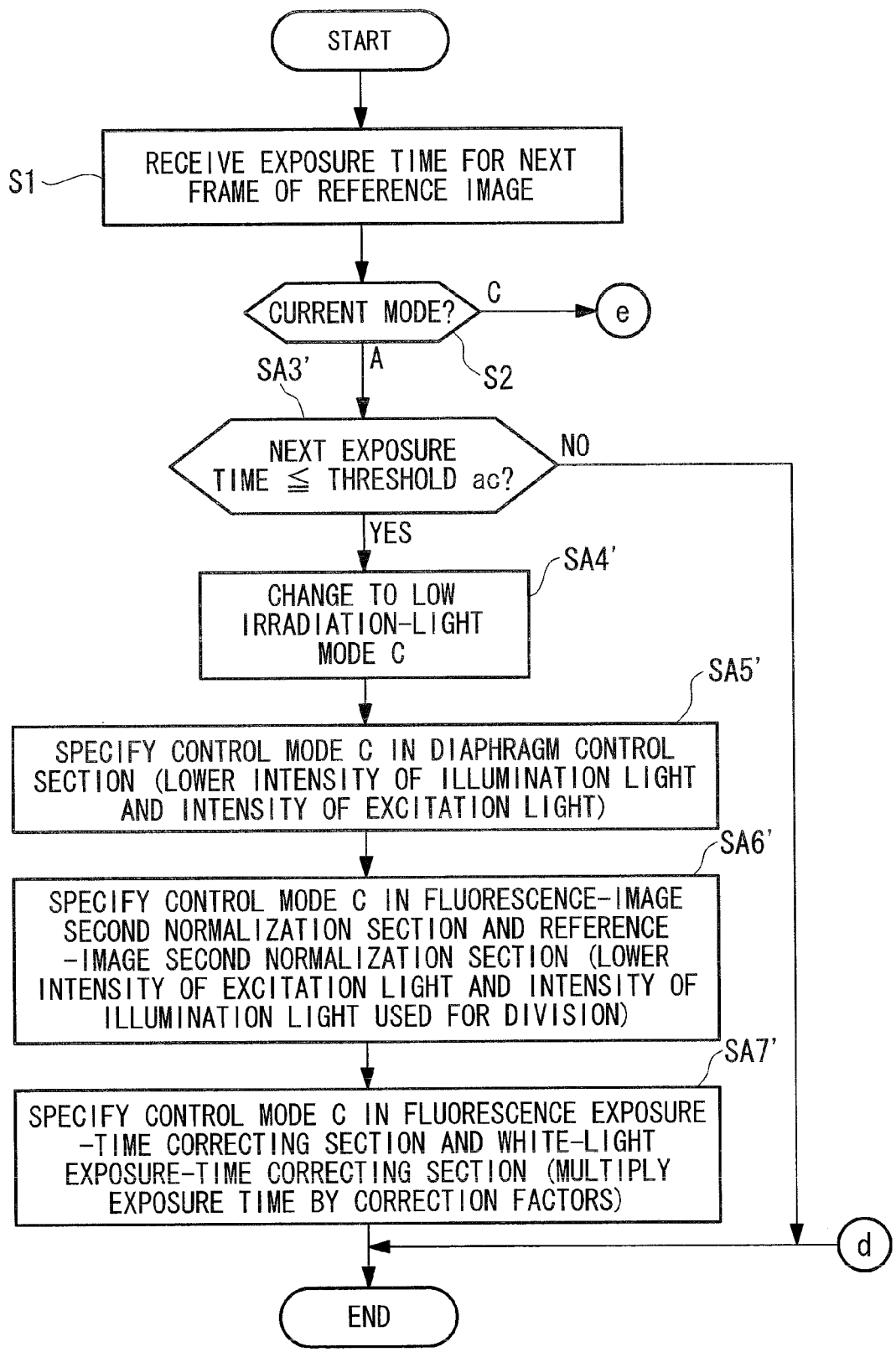
FIG. 9 is a flowchart showing a quantitativeness control procedure starting from the normal mode, performed by the quantitativeness control section shown in FIG. 7.

Control performed by the quantitativeness control section 56 in the fluorescence observation apparatus 200 of this embodiment will be described below with reference to flowcharts shown in FIGS. 9 and 10.

In the quantitativeness control section 56, when the exposure time for the next frame of the white-light image acquisition section 44 is received from the white-light exposure-time calculating section 67 (Step S1), the current control mode is determined (Step S2). As shown in FIG. 9, if the current control mode is the normal mode A ("A" in Step S2), it is first determined whether the exposure time for the next frame of the white-light image acquisition section 44 is shorter than or equal to a threshold ac (Step SA3').

Figure 11:
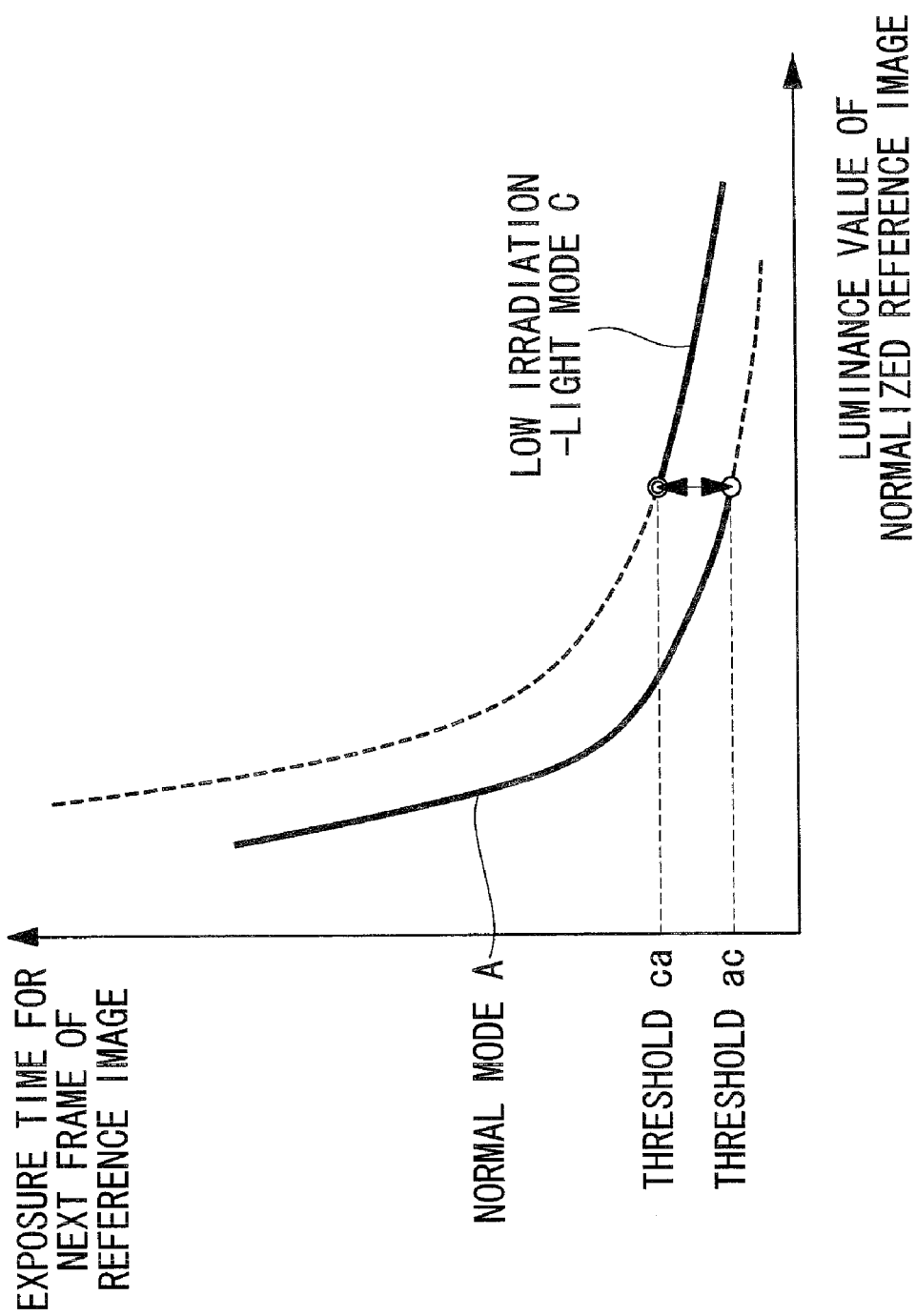
FIG. 11 is a diagram showing the relationship between the normal mode and the low irradiation-light mode, selected by the quantitativeness control section shown in FIG. 7.

If the exposure time is longer than the threshold ac ("NO" in Step SA3'), as shown in FIG. 11, the normal mode A is maintained (end). On the other hand, if the exposure time is shorter than or equal to the threshold ac ("YES" in Step SA3'), the control mode is changed to the low irradiation-light mode C (Step SA4').

In this case, the quantitativeness control section 56 outputs to the diaphragm control section 14 a control signal for switching to the low irradiation-light mode C, and the diaphragm control section 14 narrows the aperture range of the diaphragm 13 to lower the intensities of the illumination light and excitation light (Step SA5'). By lowering the intensities of the illumination light and excitation light, the intensities of illumination light and excitation light for irradiating the observation target region X are prevented from being too high.

In accordance with the lowering of the intensities of the excitation light and illumination light, the quantitativeness control section 56 outputs to the fluorescence-image second normalization section 74 and the reference-image second normalization section 78 the control signal for switching to the low irradiation-light mode C to lower the intensity of the excitation light by which the luminance value of the fluorescence image is divided and the intensity of the illumination light by which the luminance value of the reference image is divided (Step SA6'). By doing so, the quantitativeness of the normalized fluorescence image can be maintained in the fluorescence-image second normalization section 74, and that of the normalized reference image can be maintained in the reference-image second normalization section 78.

The quantitativeness control section 56 outputs to the fluorescence exposure-time correcting section 63 and the white-light exposure-time correcting section 68 the control signal for switching to the low irradiation-light mode C and specifies therein correction factors for lengthening the exposure time of the fluorescence image acquisition section 42 and the exposure time of the white-light image acquisition section 44 in order that a fluorescence image and a reference image to be acquired immediately after the intensity of the excitation light and the intensity of the illumination light are lowered will not be too dark (Step SA7'). By doing so, the exposure time for the next frame of the fluorescence image acquisition section 42 specified by the fluorescence exposure-time control section 64 and the exposure time for the next frame of the white-light image acquisition section 44 specified by the white-light exposure-time control section 69 are each corrected, and thus, the brightness of the fluorescence image and that of the reference image are maintained substantially constant.

Figure 10:
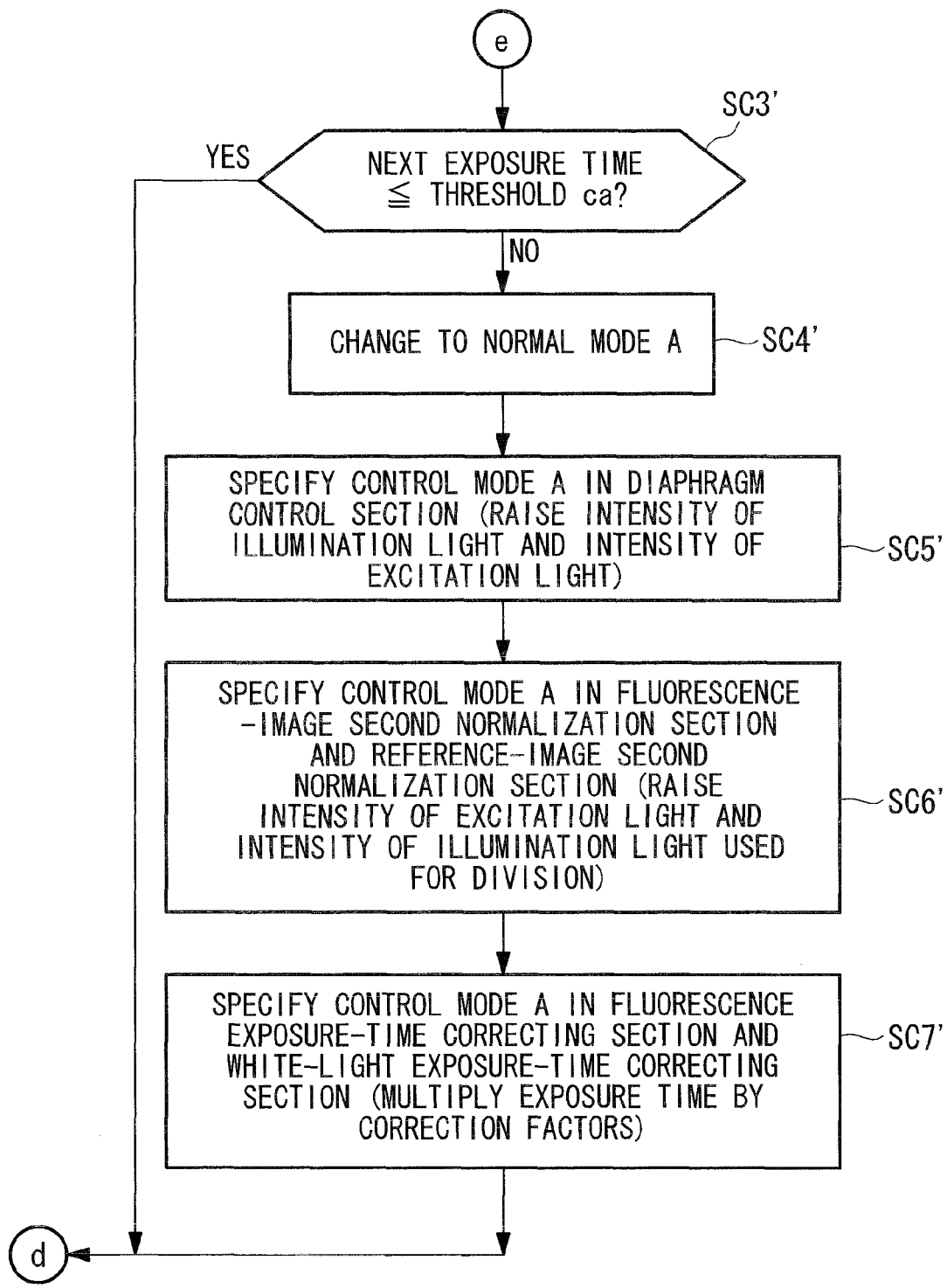
FIG. 10 is a flowchart showing a quantitativeness control procedure starting from the low irradiation-light mode, performed by the quantitativeness control section shown in FIG. 7.

Next, if the current control mode is the low irradiation-light mode C ("C" in Step S2), as shown in FIG. 10, it is determined whether the exposure time of the white-light image acquisition section 44 is shorter than or equal to a threshold ca (Step SC3'). If the exposure time is shorter than or equal to the threshold ca ("YES" in Step SC3'), as shown in FIG. 11, the low irradiation-light mode C is maintained (end). On the other hand, if the exposure time is longer than the threshold ca ("NO" in Step SC3'), the control mode is changed to the normal mode A (Step SC4').

In this case, the quantitativeness control section 56 outputs to the diaphragm control section 14 a control signal for switching to the normal mode A, and the diaphragm control section 14 expands the aperture range of the diaphragm 13 to raise the intensities of the illumination light and excitation light (Step SC5'). By raising the intensities of the illumination light and excitation light, it is possible to prevent a situation in which the reference image and the fluorescence image are dark because the intensities of the illumination light and excitation light for irradiating the observation target region X are too low.

In accordance with the raising of the intensities of the excitation light and illumination light, the quantitativeness control section 56 outputs to the fluorescence-image second normalization section 74 and the reference-image second normalization section 78 the control signal for switching to the normal mode A to raise the intensity of the excitation light by which the luminance value of the fluorescence image is divided and the intensity of the illumination light by which the luminance value of the reference image is divided (Step SC6'). By doing so, the quantitativeness of the normalized fluorescence image can be maintained in the fluorescence-image second normalization section 74, and that of the nor malized reference image can be maintained in the reference-image second normalization section 78.

The quantitativeness control section 56 outputs to the fluorescence exposure-time correcting section 63 and the white-light exposure-time correcting section 68 the control signal for switching to the normal mode A and specifies therein correction factors for shortening the exposure time for the next frame of the fluorescence image acquisition section 42 and the exposure time for the next frame of the white-light image acquisition section 44 in order that a fluorescence image and a reference image to be acquired immediately after the intensities of the excitation light and illumination light are raised will not be saturated (Step) SC7'. By doing so, the exposure time of the fluorescence image acquisition section 42 specified by the fluorescence exposure-time control section 64 and the exposure time of the white-light image acquisition section 44 specified by the white-light exposure-time control section 69 are each corrected, and thus, the brightness of the fluorescence image and that of the reference image are maintained substantially constant.

This embodiment can be modified as follows.

Figure 12:
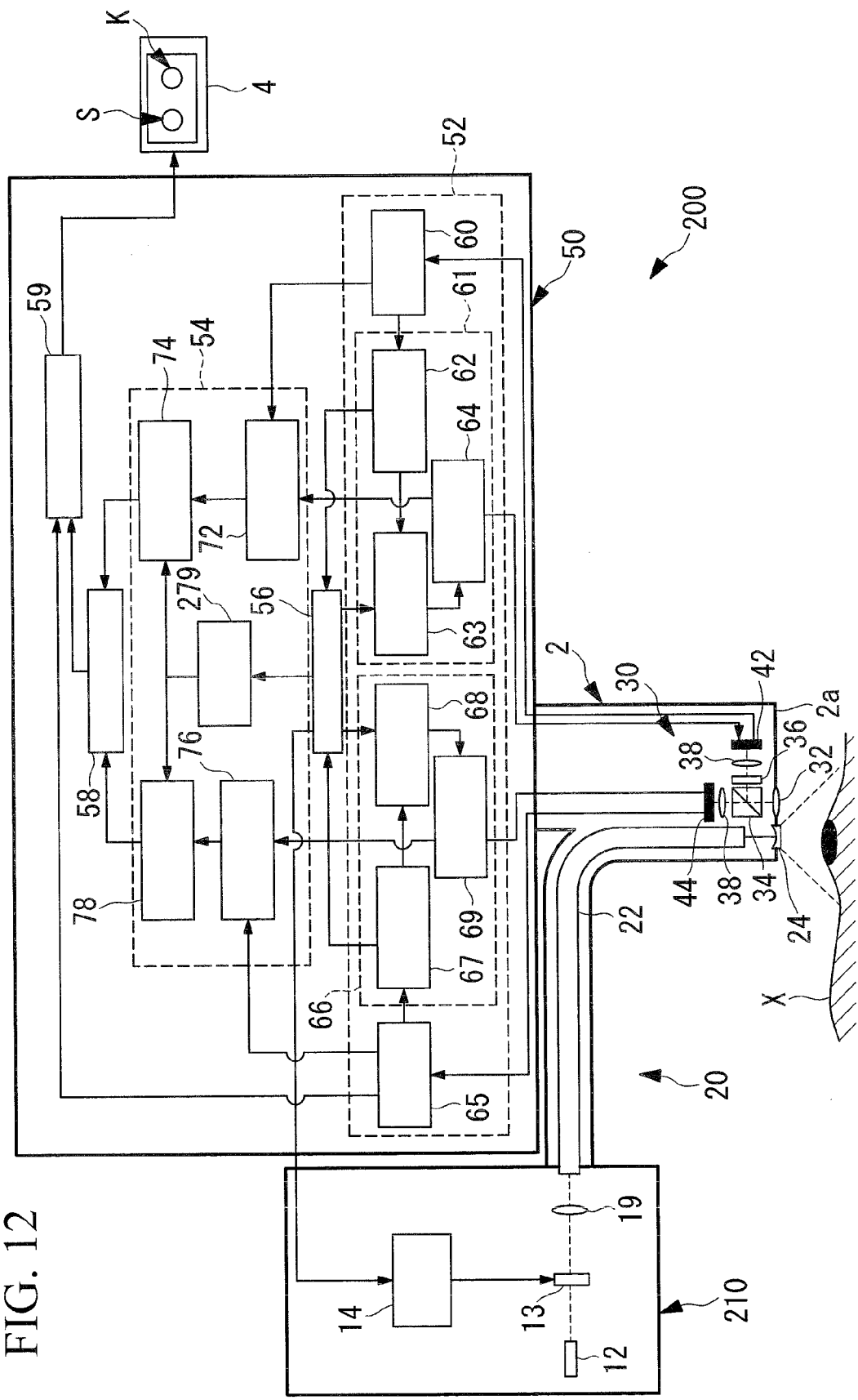
FIG. 12 is a block diagram showing, in outline, the configuration of a fluorescence observation apparatus according to a modification of the second embodiment of the present invention.

For example, as shown in FIG. 12, the luminance normalization unit 54 may include a luminous intensity distribution characteristic correction section (intensity correction section) 279 that corrects the intensities of the excitation light and illumination light corresponding to the control mode input from the quantitativeness control section 56 to the fluorescence-image second normalization section 74 and the reference-image second normalization section 78, based on the intensity distribution characteristics (in other words, luminous intensity distribution characteristics) of the excitation light and the intensity distribution characteristics of the illumination light, respectively.

In this case, the luminous intensity distribution characteristic correction section 279 just needs to multiply the light intensity by a different correction factor for each pixel of the fluorescence image and the reference image. By doing so, when the diaphragm control section 14 changes the intensity of the illumination light and the intensity of the excitation light, even if the light intensity distribution characteristics of the excitation light and the light intensity distribution characteristics of the illumination light change in different ways from each other because of a difference in wavelength band between the illumination light and the excitation light, the intensity of the excitation light and the intensity of the illumination light changed by the diaphragm control section 14 are corrected by the luminous intensity distribution characteristic correction section 279, and the luminance of the fluorescence image and the luminance of the reference image can be accurately normalized in the fluorescence-image second normalization section 74 and the reference-image second normalization section 78, respectively, thus enhancing the quantitativeness of the fluorescence image.

The embodiments of the present invention have been described above in detail with reference to the drawings; however, specific configurations are not limited to these embodiments, and design changes that do not depart from the scope of the present invention are also included. For example, the application of the present invention is not limited to the above-described embodiments and modification, and the present invention can be applied to an embodiment in which these embodiments and modification are appropriately combined, and the combination thereof is not particularly limited.

For example, in the above-described embodiments and modification, the intensity of the illumination light and the intensity of the excitation light are controlled; however, the intensity of at least one of the illumination light and excitation light just needs to be controlled. Furthermore, the luminance of at least one of a fluorescence image and a reference image just needs to be normalized by the exposure time. Furthermore, the luminance of at least one of a fluorescence image and a reference image just needs to be normalized by the light intensity. Furthermore, in the luminous intensity distribution characteristic correction section 279, the intensity of at least one of the illumination light and excitation light just needs to be corrected based on the intensity distribution characteristics of the at least one of the illumination light and excitation light.

For example, in the above-described embodiments and modification, a description has been given in which near-infrared fluorescence and white light are used as examples; however, the type of light is not limited thereto. For example, visible-region fluorescence may be used instead of near-infrared fluorescence, and visible-region excitation light may be used instead of white light.

In the above-described embodiments and modification, a description has been given in which the three control modes A, B, and C and the thresholds ab, bc, cb, ac, and ca are used as examples; however, the types are not limited thereto. For example, the control mode may be divided into four modes or more. Furthermore, for example, a threshold used to determine whether to change the intensity of excitation light may be set larger than a threshold used to determine whether to change the intensity of illumination light.

For example, in the above-described embodiments, a description has been given in which the xenon lamp 12 is used as a light source; however, instead of this, a mercury lamp may be employed, for example.

In the above-described embodiments, the diaphragm 13 is used to control the intensity of the illumination light; however, instead of this, for example, a variable ND filter may be employed, or the input current value of the xenon lamp 12 (or a mercury lamp) may be adjusted.

In the above-described embodiments, a description has been given in which the input current value of the semiconductor laser 16 is adjusted to control the intensity of the excitation light; however, instead of this, for example, a diaphragm or a variable ND filter may be employed, or a diffraction grating may be employed. When a diffraction grating is employed, the intensity of excitation light can be changed by using either the first-order diffraction light or the second-order diffraction light of the diffraction grating as excitation light.

A plurality of LEDs may be employed as a light source. In this case, the light intensity may be controlled by employing a diaphragm or a variable ND filter or by adjusting the input current value, or the light intensity may be controlled by changing the number of LEDs to be turned on.

What is claimed is:

1. A fluorescence observation apparatus comprising:
    an illumination section that includes a light source for irradiating a subject with illumination light and excitation light;
    a fluorescence image acquisition section that acquires a fluorescence image from fluorescence produced in the subject irradiated with the excitation light emitted from the illumination section;
    a return-light image acquisition section that acquires a reference image from return light returning from the subject irradiated with the illumination light emitted from the illumination section;
    an exposure-time adjustment section that adjusts exposure time based on a luminance value of the reference image acquired by the return-light image acquisition section;
    an illumination control section that controls the intensity of at least one of the illumination light and the excitation light emitted from the illumination section, based on the exposure time adjusted by the exposure-time adjustment section;
    first normalization section that normalizes the luminance of at least one of the reference image and the fluorescence image by the exposure time;
    second normalization section that normalizes the luminance of the at least one of the reference image and the fluorescence image by the intensity of the at least one of the illumination light and the excitation light controlled by the illumination control section; and
    an image correction section corrects the fluorescence image by the reference image, by using at least one of the reference image or the fluorescence image normalized by the first normalization section and the second normalization section.

2. A fluorescence observation apparatus according to claim 1, wherein the image correction section divides the fluorescence image by the reference image.

3. A fluorescence observation apparatus according to claim 1, wherein the exposure-time adjustment section corrects the exposure time such that the brightness of the at least one of the reference image acquired from the illumination light and the fluorescence image acquired from the excitation light, whose intensity has been controlled by the illumination control section, is maintained constant.

4. A fluorescence observation apparatus according to claim 1, further comprising intensity correction section that corrects the intensity of the at least one of the reference image and the fluorescence image by which the luminance of the at least one of the illumination light and the excitation light is normalized by the second normalization section, based on the corresponding light intensity distribution characteristics.

* * * * *